US 8,846,337 B2

(12) United States Patent
Schann et al.

(10) Patent No.: US 8,846,337 B2
(45) Date of Patent: Sep. 30, 2014

(54) DEVICE FOR SPRAYING A REAGENT FOR FAST MICROBIOLOGICAL ANALYSIS

(71) Applicant: EMD Millipore Corporation, Billerica, MA (US)

(72) Inventors: Christian Schann, Oberhausbergen (FR); Bruno Duquet, Acton, MA (US); Abdel Hajila, Obernal (FR); Frederic Olivieri, Barr (FR)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 14/047,373

(22) Filed: Oct. 7, 2013

(65) Prior Publication Data

US 2014/0038226 A1    Feb. 6, 2014

Related U.S. Application Data

(62) Division of application No. 13/868,263, filed on Apr. 23, 2013, which is a division of application No. 12/004,784, filed on Dec. 20, 2007.

(30) Foreign Application Priority Data

Jan. 29, 2007 (FR) ..................... 07 52949

(51) Int. Cl.
*G01N 21/76* (2006.01)
*B05B 15/04* (2006.01)
*C12Q 1/24* (2006.01)

(52) U.S. Cl.
CPC ............... *C12Q 1/24* (2013.01); *B05B 15/045* (2013.01); *G01N 21/763* (2013.01)
USPC ............................................. 435/34

(58) Field of Classification Search
CPC ....... C12Q 1/24; G01N 21/763; B05B 15/045
USPC .................................... 435/30, 34
See application file for complete search history.

(56) References Cited

U.S. PATENT DOCUMENTS

| | | | |
|---|---|---|---|
| 3,550,857 A | 12/1970 | Ahlberg | |
| 3,583,634 A | 6/1971 | Sheetz | |
| 3,756,514 A | 9/1973 | Brown | |
| 4,478,370 A | 10/1984 | Hastings | |
| 5,766,868 A | 6/1998 | Seto | |
| 6,113,008 A | 9/2000 | Arsenault et al. | |
| 2005/0023377 A1 | 2/2005 | Kawamoto | |
| 2006/0219816 A1 | 10/2006 | Herre et al. | |
| 2008/0179425 A1 | 7/2008 | Schann et al. | |
| 2013/0236926 A1 | 9/2013 | Schann et al. | |

FOREIGN PATENT DOCUMENTS

| | | |
|---|---|---|
| DE | 660924 C | 5/1938 |
| NL | 6906136 A | 10/1970 |
| WO | 2005/075015 A1 | 8/2005 |
| WO | 2006/000730 A1 | 1/2006 |

OTHER PUBLICATIONS

Ramshackle Glam, Side Table Rehab/Yay! DIY, Step 5, Accessed Feb. 14, 2014 online at: www.ramshackleglam.com/2011/03/28/guest-post-yay-diy, 11 pages, by Jordan Reid.
The Bearfoot Baker, Airbrush with Stencils, Mar. 24, 2013, available online at: thebearfootbaker.com/2013/03/how-to-airbrush-with-stencils, 10 pages.
eHow, How to Use Stencil Bricks and Add Star Flair in Airbrushing, Accessed Feb. 14, 2014, online at: www.ehow.com/how_2215121_use-stencil-bricks-add-star.html, 4 pages.
Final Rejection mailed Feb. 26, 2014 in corresponding U.S. Appl. No. 13/868,263.
French Search Report dated Sep. 18, 2007 in corresponding French patent application No. FR 0752949.
Office Action mailed Mar. 25, 2011 in corresponding U.S. Appl. No. 12/004,784.
Final Rejection mailed Jul. 20, 2011 in corresponding U.S. Appl. No. 12/004,784.
Office Action mailed Aug. 13, 2013 in corresponding U.S. Appl. No. 12/004,784.
Final Rejection mailed Oct. 21, 2013 in corresponding U.S. Appl. No. 12/004,784.
Advisory Action mailed Dec. 16, 2013 in corresponding U.S. Appl. No. 12/004,784.
Office Action—Restriction—mailed Sep. 10, 2013 in corresponding U.S. Appl. No. 13/868,263.
Office Action mailed Nov. 1, 2013 in corresponding U.S. Appl. No. 13/868,263.
Notice of Allowance mailed Apr. 24, 2014 in corresponding U.S. Appl. No. 12/004,784.
Notice of Allowance mailed Jun. 2, 2014 in corresponding U.S. Appl. No. 12/004,784.
Notice of Allowance mailed Aug. 1, 2014 in corresponding U.S. Appl. No. 13/868,263.

*Primary Examiner* — Karen Cochrane Carlson
*Assistant Examiner* — Jennifer M. H. Tichy
(74) *Attorney, Agent, or Firm* — Nields, Lemack & Frame, LLC (57) ABSTRACT

The device for spraying a reagent onto a support (81) adapted to retain microorganisms on a predetermined surface (82), comprises a spraying bell (3) as well as a nozzle (71) for emitting a jet of droplets of said reagent into a spraying chamber (34) comprised by said bell (3), said device also comprising an absorbent pad (5) mounted against said bell (3) transversely to said jet and closing said chamber (34) from the opposite side to said nozzle (71) with the exception of a circular central opening (51) provided in said pad (5), the diameter of said central opening (51) being adapted to enable a portion of said jet, when said device faces said support (81) and is at a predetermined distance therefrom, to pass through said central opening (51) over its entire area and be deposited on the whole of said predetermined surface (82) of said support (81).

4 Claims, 6 Drawing Sheets

DEVICE FOR SPRAYING A REAGENT FOR FAST MICROBIOLOGICAL ANALYSIS

This application is a divisional of U.S. Ser. No. 13/868,263 filed Apr. 23, 2013, which is a divisional of U.S. Ser. No. 12/004,784, filed Dec. 20, 2007, which claims priority of French application No. 0752949 filed Jan. 29, 2007, the disclosures of which are hereby incorporated by reference.

The present invention concerns a spraying device for fast microbiological analysis.

At present, checking the microbiological quality of liquids, gases or surfaces in the context of industrial and medical activities has to conform to strict standards.

On account of this, the industrial players and health authorities must have tools at their disposal making it possible to detect microbiological contaminations as soon as possible, in order to be able to correct these in good time and at reduced cost.

In practice, microbiological monitoring is carried out on a gel growth medium where microorganisms, after having been collected on a microporous membrane, are cultured until they have been rendered visible to the naked eye.

The incubation periods vary from one microorganism to another but are in general at least 24 hours and sometimes more for slower growth microorganisms (such as mycobacteria) or because the microorganisms have been stressed by environmental conditions.

To render the detection more rapid, another approach consists of reducing the minimum duration of culture (or even, for some microorganisms, of eliminating it completely) by basing the detection of the microorganisms on their metabolic activity.

A universal metabolic marker, most commonly adenosine triphosphate (ATP) contained in living microorganisms, is measured by bringing it into contact with a reagent revealing the presence of ATP by luminescence (termed a "bio luminescence reagent") which enables the presence of microorganisms to be noticed without having to wait for colonies to form on a gel growth medium and to become visible to the naked eye.

The quantity of light emitted is a function of the mass of ATP and thus the number of microorganisms.

A device for detection by fast microbiology is already known which is commercialized by the applicant under the name Milliflex Rapid®, and which comprises:

- a station for filtering a volume of liquid onto a membrane so as to capture the microorganisms that may be contained in the liquid on the membrane;
- a station for spraying a reagent revealing the presence of ATP by luminescence facing which the operator places the membrane, after the filtering step and after having rendered the ATP of the microorganisms accessible (by a step of lysis of the microorganisms for example), for the reagent to be deposited; and
- a station for measuring the quantity of light emitted in response to the depositing of the reagent revealing the presence of ATP by luminescence, facing which the operator places the membrane, after the spraying step, the light emitted by the membrane being collected by a CCD camera and processed and then analyzed to detect the presence of microorganisms on that membrane.

The spraying station is provided with a spraying device comprising a sprayer spraying droplets emitted in the form of a jet onto the membrane in the ambient air situated above the membrane.

The invention concerns the provision of a device of the same type that both has better performance and is more practical while remaining reliable in terms of the risks of contaminations of the support to analyze.

To that end it provides a device for spraying a reagent onto a support for the fast microbiological analysis of said support, said support being adapted to retain microorganisms on a predetermined surface, characterized in that said device comprises a spraying bell as well as a nozzle for emitting a jet of droplets of said reagent into a spraying chamber comprised by said bell, said device also comprising an absorbent pad mounted against said bell transversely to said jet and closing said chamber from the opposite side to said nozzle with the exception of a circular central opening provided in said pad, the diameter of said central opening being adapted to enable a portion of said jet, when said device faces said support and is at a predetermined distance therefrom, to pass through said central opening over its entire area and be deposited on the whole of said predetermined surface of said support.

The spraying device according to the invention, provided with a bell and an absorbent pad used in combination, makes it possible to keep the (relatively volatile) droplets of the sprayed jet confined such that it is thus possible to group together the measuring station and the spraying station into the same analysis chamber.

More particularly, in the absence of effective confinement of the jet of droplets, such grouping together would be rendered impossible since those (relatively volatile) droplets would risk being deposited on the entire surface of the analysis chamber including the measuring station. As this chamber may be contaminated by extraneous ATP (ATP which is naturally present on the surfaces), putting the reagent in contact with that extraneous ATP would generate light which would risk perturbing the analysis of that emitted by the support.

Furthermore, the pad of this device is shaped so as to collect the droplets situated at the periphery of the jet and liable to enter into contact with the bell. This is because it is particularly important to trap those droplets since, having entered into contact with the bell (which may also be contaminated by extraneous ATP), they constitute potential sources of contamination of the support by extraneous ATP if the paths of those droplets were to end their travel on that support.

The pad thus makes it possible to select only the portion of the jet of droplets adapted to uniformly cover the whole of the surface of the support to analyze, without risk of contaminating it.

Furthermore, the diameter of the opening of the pad, which is a function of the distance to the support from the pad, means that the beam of sprayed droplets leaving by the opening of the pad over the entire area of that opening uniformly covers the entire surface to treat of the support and solely that surface in order to avoid any risk of contamination by the droplets coming into contact with the environment close to the support.

According to features that are preferred for reasons of simplicity and convenience of use, said spraying chamber is delimited by a wall substantially transverse to said jet, facing said pad and at the center of which is disposed said nozzle, by a side wall of which one edge joins to the periphery of said substantially transverse wall, as well as by said pad disposed against said side wall;

According to still other features that are preferred for the same reasons as above, said side wall has at least one frusto-conical portion against which is disposed said pad and of which the taper is adapted to orientate the droplets which are at the periphery of said jet towards said pad.

That frusto-conical portion enables the droplets which do not have sufficient energy to rebound to flow along that portion and then to be absorbed by the pad and, for those which have sufficient speed to rebound, to orientate the rebounds towards the pad itself but not in the direction of its central opening such that those droplets are also trapped by the pad.

According to still other preferred features:

said side wall comprises, between said transverse wall and said frusto-conical portion against which is disposed said pad, an intermediate portion also adapted to orientate the droplets which are at the periphery of said jet towards said pad and of lesser taper than that of said frusto-conical portion against which is disposed said pad;

said transverse wall comprises a frusto-conical portion of taper between that of said intermediate portion and that of said frusto-conical portion against which is disposed said pad; and/or said device also comprises a ring for retaining said pad against said bell.

According to still other preferred features, at the center of said ring, there is provided a circular opening of greater diameter than the diameter of the opening provided in said pad.

Figure 1:
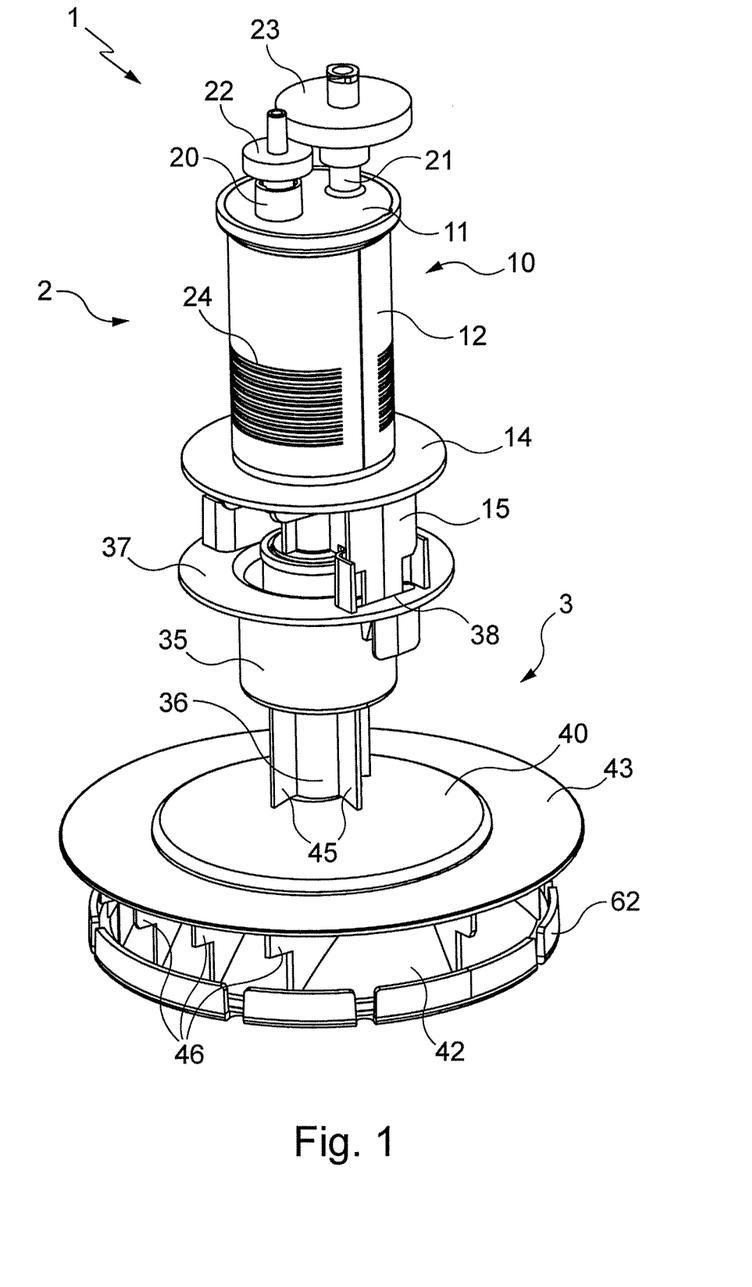
Figure 2:
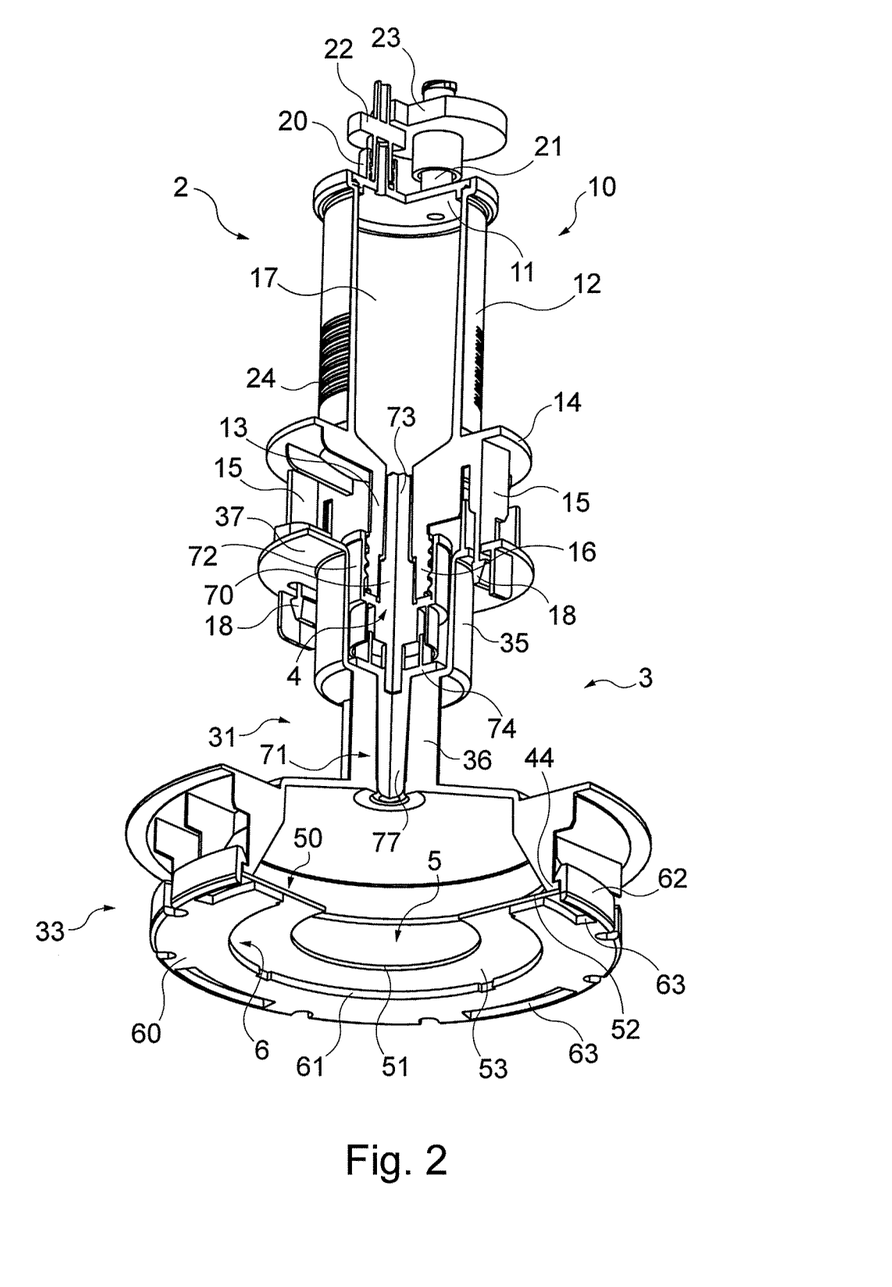

The difference in diameter means that a portion of the pad is visible from the support such that in case the droplets strongly rebound on the support they land and are trapped on the pad and not on the ring (since in that case they would risk falling back onto the support, carrying extraneous ATP).

According to still other preferred features:

- said ring has snap-fitting means adapted to cooperate with complementary snap-fitting means comprised by said bell;
- said device also comprises a reservoir and a pump disposed between said nozzle and said reservoir;
- said reservoir is slidingly mounted relative to said bell, said pump being adapted to make a said jet of droplets come out of said nozzle on sliding of said reservoir in the direction of said bell;
- said reservoir comprises a body provided with an annular bearing collar; and/or
- said reservoir has snap-fitting means adapted to cooperate with complementary snap-fitting means comprised by said bell.

The features and advantages of the invention will appear from the following description, given by way of preferred but non-limiting example, with reference to the accompanying drawings in which:

FIG. 1 is a perspective view of a spraying device according to the invention;

FIG. 2 is a view similar to FIG. 1 but with part of the device cut away;

FIG. 3 is an elevation view in section taken along a median plane of symmetry of the device and of a filter cassette provided with a microporous membrane to analyze disposed under the device using a robot arm;

FIG. 4 is a similar view to FIG. 3 but in which a liquid reservoir of the device is represented in the position it occupies after sliding towards a spraying bell of the device to actuate the ejection of a jet of droplets;

FIG. 5 is an enlarged view of the filter cassette and of the end of the spraying device which faces the cassette, in which arrows show different possible paths for the droplets of sprayed reagent; and FIG. 6 is a perspective view of the device into which a protective plug has been fitted, this assembly being placed in a packaging tray.

The spraying device 1 illustrated in FIGS. 1 and 2 comprises a reservoir 2, a confinement bell 3, a spraying unit 4, a porous pad 5 and a fixing ring 6 (FIG. 2).

The reservoir 2 is slidingly mounted relative to the bell 3 and comprises a body 10 of plastics material as well as a cover 11.

The body 10 has a first cylindrical portion 12, a second cylindrical portion 13, an annular collar 14 and two legs 15.

The cylindrical portion 12 delimits a housing 17 for receiving the reagent which is obturated by the cover 11.

The cylindrical portion 13 is situated in line with the portion 12 on the opposite side to the cover 11 and has an outer diameter less than that of the portion 12.

A screw thread 16 is formed in the neighborhood of the opposite end of portion 13 to that connected to portion 12.

The collar 14 is transversely attached to the rest of the body at the junction of portions 12 and 13.

The two legs 15 which are diametrically opposite each other project from the opposite side of the collar to the cover 11 Each leg has a tooth 18 projecting from the opposite side to the other leg 15.

The cover 11 has two ducts 20 and 21.

A filter unit 22 (and respectively 23) is screwed into duct 20 (and respectively duct 21).

The filter unit 22 is an air filter whereas unit 23 is a liquid filter.

Means 24 for identification of the reagent and/or of the device may be stuck or engraved around the reservoir.

The confinement bell 3 is of plastics material formed as a single piece.

The bell comprises a first portion 31 (FIG. 3) delimiting a housing 32 for receiving the spraying unit 4 and a second portion 33 delimiting together with the pad 5 a spraying and confinement chamber 34.

Portion 31 of the bell is formed from a first cylindrical portion 35, from a second cylindrical portion 36 and from an annular collar 37.

Portion 35, which is of greater diameter than portion 36, is joined by one end to that portion (portions 35 and 36 being in line with each other) and by the other end to the collar 37, the latter being connected transversely to portion 35.

Collar 37 has two diametrically opposite oblong apertures 38 (FIG. 1) into which the legs 15 of the reservoir are snap fitted.

In the snap-fitted state of the reservoir in the bell, the collars 14 and 37 face each other with the teeth 18 of the snap-fitting feet 15 being situated on the opposite side of the collar 37 to the collar 14.

Portion 33 of the bell has a significantly flared first frusto-conical portion 40, a second very slightly flared portion 41 (here this portion is practically cylindrical, its taper is practically nil) and a third portion 42 also frusto-conical and of moderate degree of flare, against which the pad 5 is disposed.

The degree of taper of portion 40 is thus greater than that of portion 41 and less than that of portion 42.

Cylindrical portion 35 is joined to portion 40 via portion 36. Portion 40 forms a wall substantially transverse to the direction of spraying of the reagent and faces the pad 5 whereas portions 41 and 42 form a lateral wall extending from the periphery of portion 40 to the pad 5.

This portion also comprises an annular collar 43 transversely connected to portion 41 as well as an annular lip 44 connected to the opposite peripheral end of portion 42 to that joined to portion 41.

The bell is also provided with reinforcing fins 45 at portion 36 and reinforcing fins 46 at portion 42 that are attached to collar 43 (FIG. 1).

The absorbent pad 5, visible in FIG. 2, is of cellulose wadding and takes the form of a disc 50 in which a circular central opening 51 is formed. The pad is disposed against the lip 44 of portion 42 and closes the spraying chamber 34 except for the central opening 51 which enables said chamber to communicate with the outside of the device.

The ring 6 is of plastics material and takes the form of a disc 60 in which a circular opening 61 is formed at its center and is provided with a snap-fitting collar 62 at its periphery.

The ring also has a series of cut-outs 63 at its periphery. Pad 5 is disposed between the lip 44 and the ring 6 with the ring snap fitted against the lip.

The diameter of the opening 51 here is 40 mm whereas the diameter of the opening 61 is 65 mm such that the pad has a portion 52 (FIG. 2) hidden by portion 60 and a portion 53 which projects inwardly of the bell and which is not covered by portion 60 of ring 6.

The spraying unit 4 comprises a pump 70 and a spraying nozzle 71 as well as a screw-fitting plug 72 which are illustrated in FIG. 2.

Via a duct 73 the pump communicates on one side with the housing 17 of the reservoir and on the other side with the nozzle 71, the duct 73 continuing through the nozzle so as to issue in the housing 34 of the bell (FIG. 2).

The plug 72 as well as the pump 70 are disposed in the housing 32 (FIG. 3) within portion 35, with the plug 72 screwed into the screw thread 16 of the cylindrical portion 13.

Figure 3:
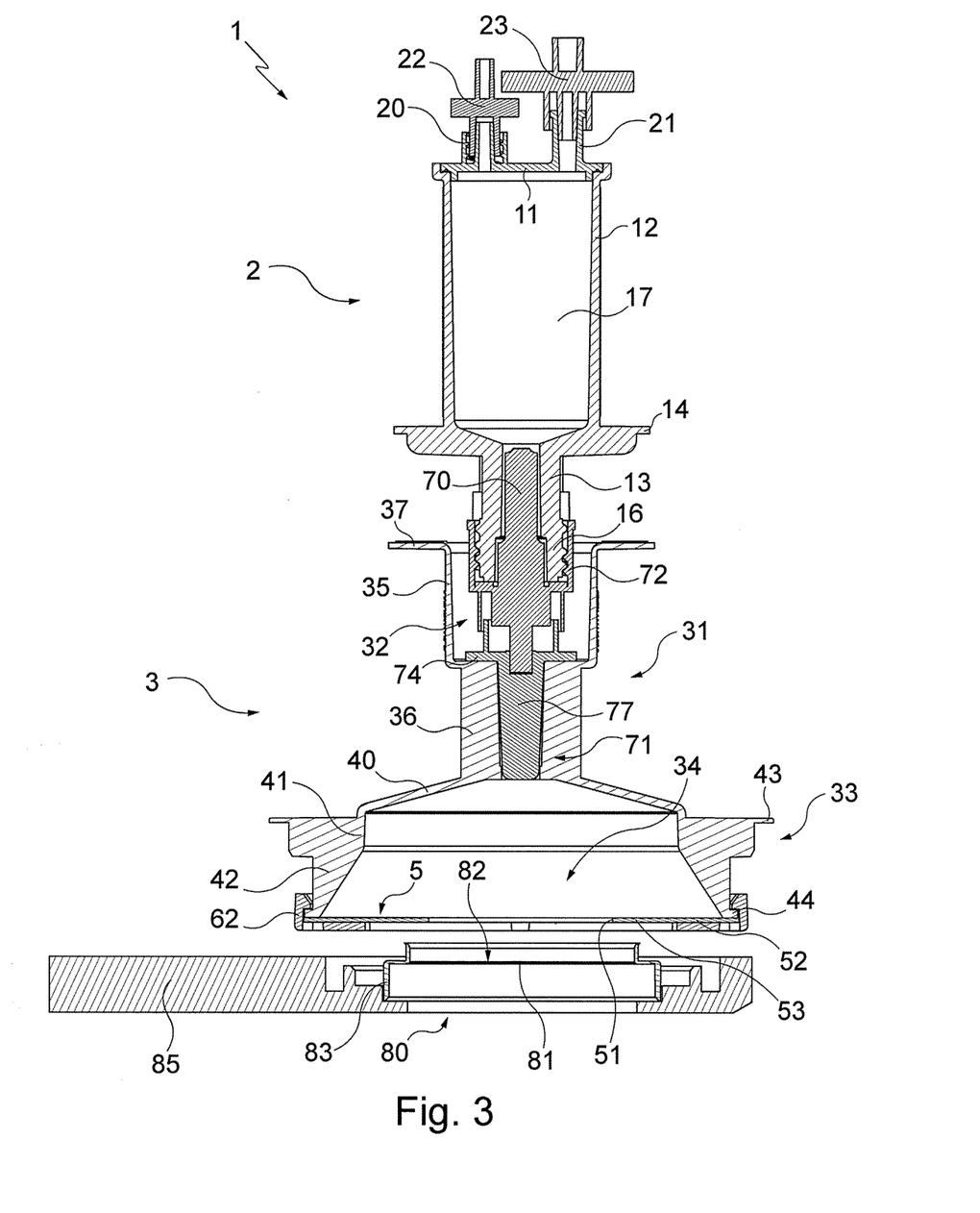

Nozzle 71 has a frusto-conical portion 77 housed in portion 36 of which one end issues in the confinement housing 34 as well as an annular collar 74 transversely connected to the opposite end of the frusto-conical portion to that emerging in housing 34, which abuts against portion 36 (FIG. 3).

Nozzle 71 is provided to emit a jet of microscopic droplets by mechanical actuation of the pump 70 engaged by a sliding movement of the reservoir 2 towards the bell 3 while bearing on the collar 14 (for example with the assistance of a robot arm).

Figure 6:
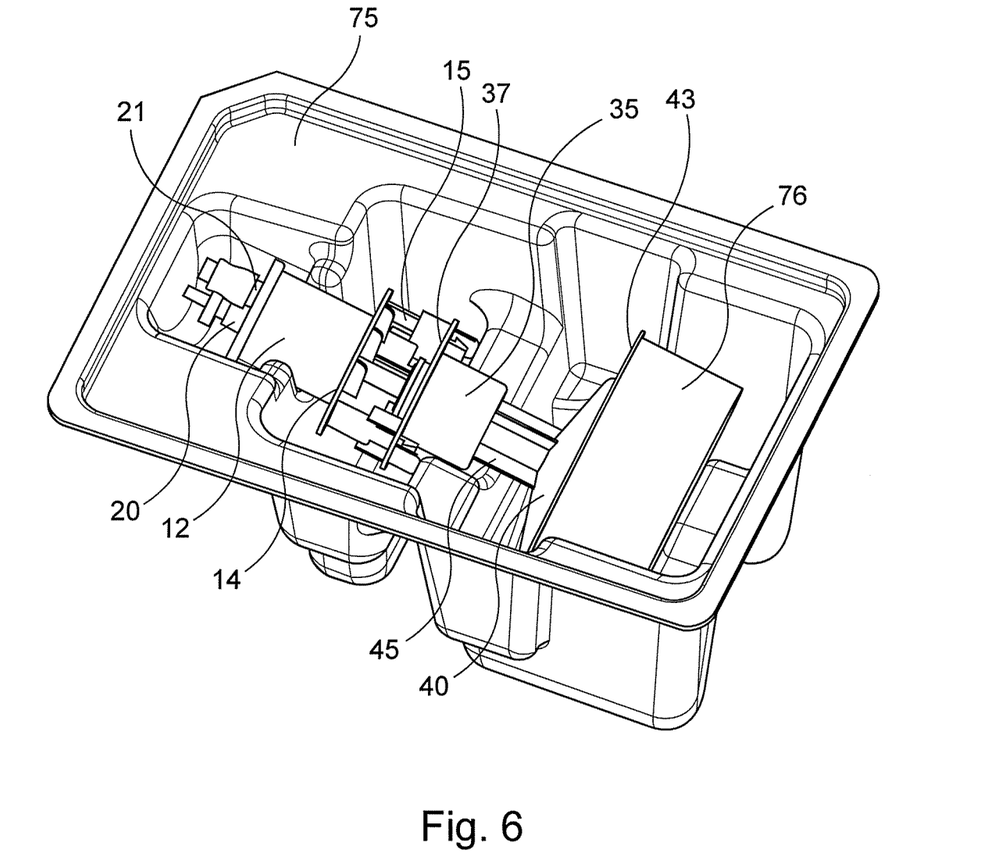

Device 1 is delivered in the packaging illustrated in FIG. 6 and takes the form of a rigid tray 75 provided with a cover (not shown), a cylindrical plug 76 being engaged around the bell, the plug abutting against the collar 43 in order to protect the confinement chamber.

Figure 4:
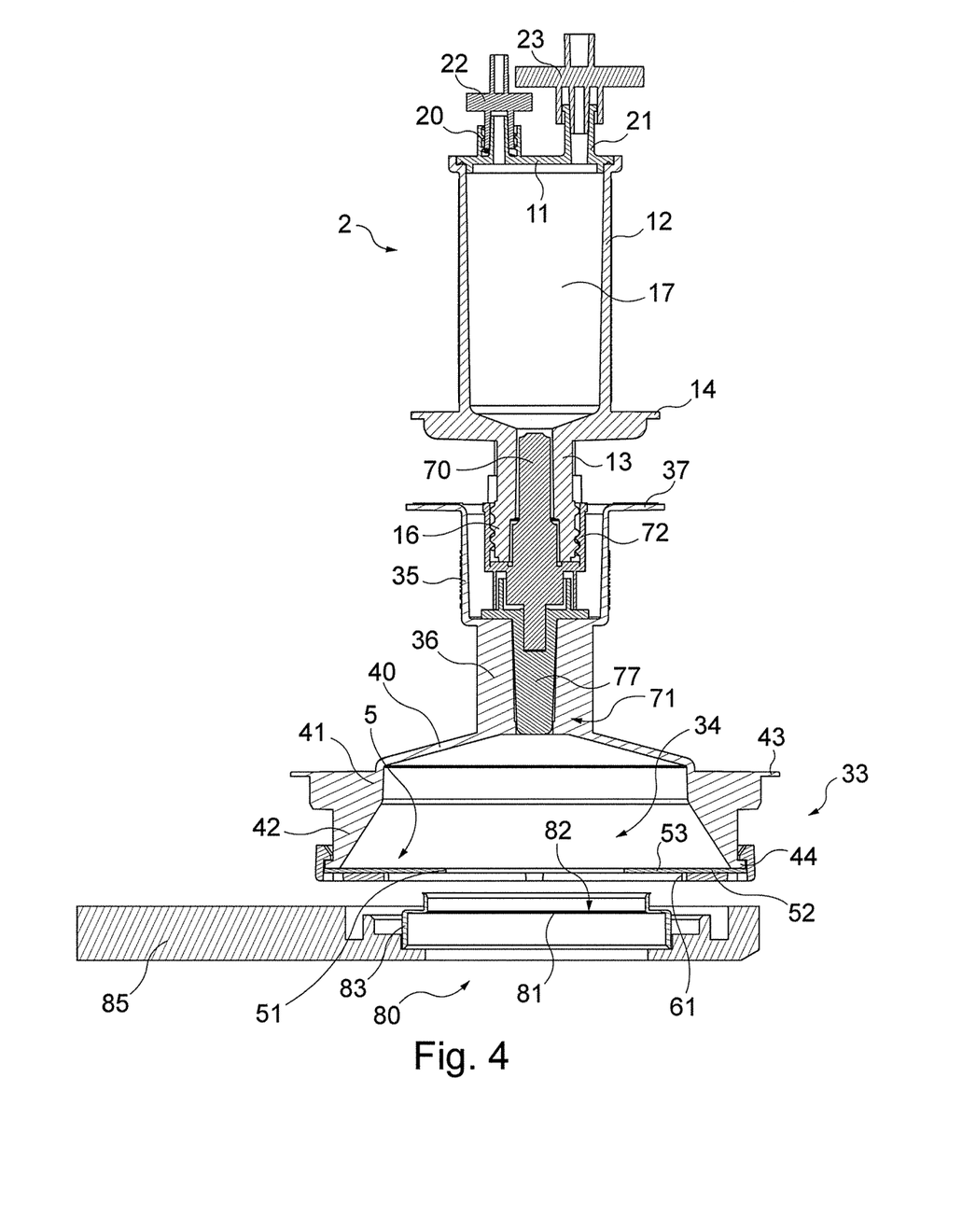
Figure 5:
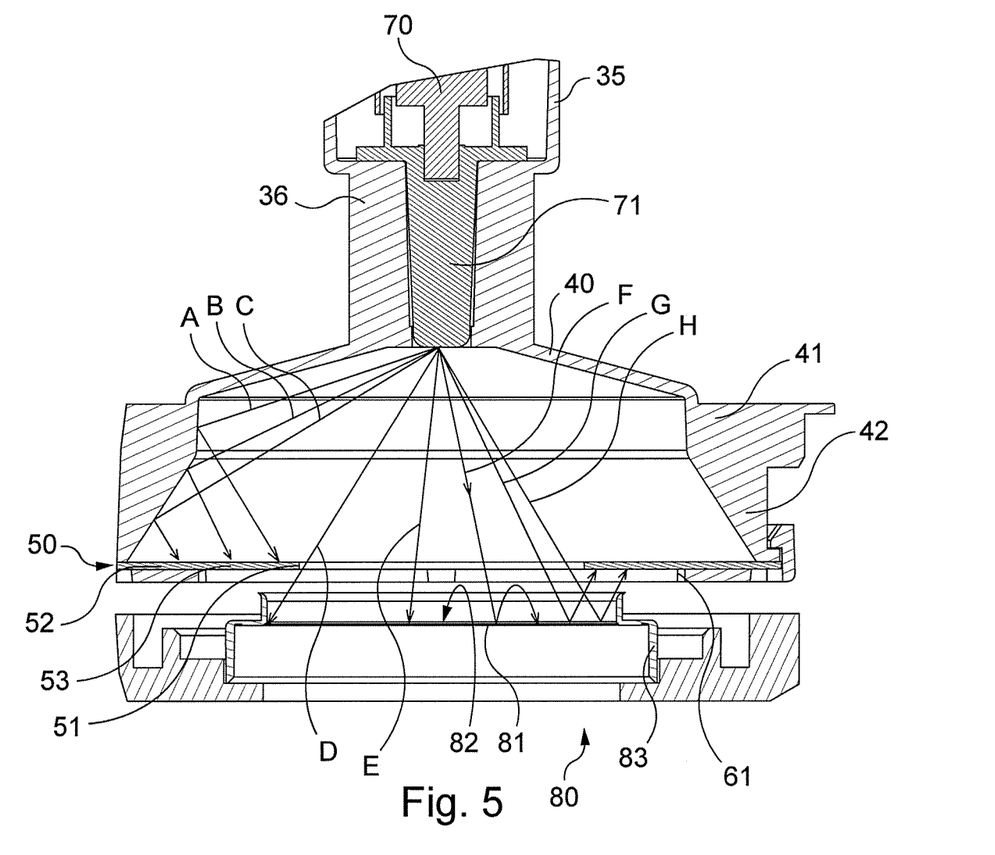

A description will now be given with the help of FIGS. 3 to 5 of how the reagent contained in the reservoir of the device is deposited on a support in the form of microscopic droplets.

The support illustrated here is a cassette 80 comprising a filter membrane 81 having useful surface 82 corresponding to a diameter equal to 49 mm and a body 83 surrounding the membrane 81.

Once the filtration of the microorganisms has been made onto the membrane 81 and after having made the ATP of the microorganisms retained on the surface 82 accessible (for example by a step of lysis of the microorganisms), the cassette 80 is placed, with the assistance of a robot arm 85 (FIG. 3) under the spraying device 1 at a predetermined distance (here 19 mm) from the absorbent pad 5. This device, from which the plug 76 has been removed beforehand, is fixedly held to a frame (not shown) of the analysis device.

A motorized unit (not shown) is then actuated to bear against the collar 14 of the reservoir so as to make the reservoir 2 slide towards the bell 3, the latter remaining immobile (FIG. 4), and so causing the actuation of the pump 70 to eject a jet of microscopic droplets into the chamber 34 through the nozzle 71.

The motorized unit is then actuated to release the pressure it exerts on the collar 14 so as to allow the reservoir 2 to resume its initial position relative to the bell 3 (FIG. 3) so as to be ready to perform a new spraying operation.

The majority of the micro-droplets cross the bell through the openings 51 and 61 without entering into contact with either the bell or the absorbent pad, those droplets being deposited onto the support evenly and homogenously over the entire useful surface 82 to be analyzed.

The diameter of the opening 51 and the distance from the pad 5 relative to the surface 82 are thus determined on the basis of the spatial dimensions of the jet of droplets in order for a high proportion (approximately 90%) of those droplets to pass through the opening 51 of the pad 5 over the entire area of that opening before being deposited on the entire surface 82.

A small proportion of the micro-droplets (the remaining 10%), situated at the periphery of the jet, are stopped by the absorbent pad 5 by entering directly into contact with it or else after having encountered the internal surfaces of the portions 40 to 42 of the bell and after having flowed along them to the pad 5 or after having rebounded on that surface so as to land on the pad 5.

More particularly and as illustrated in FIG. 5, in which different possible paths of the droplets are represented by the arrows A to H, the taper of the portions 40 to 42 is chosen such that, whatever the location at which the droplet rebounds, it is directed after its rebound towards portions 52 and 53 of the absorbent pad 5 and not in the direction of the central opening 51.

This is because the coming into contact of the droplets with the bell leads to a risk of potential contamination by the extraneous ATP that may be present on the bell such that it is sought to trap in the absorbent pad 5 all those droplets (paths A to C) in order to avoid them falling back onto the membrane 81 carrying extraneous ATP which they may have captured on the bell.

It will be noted that the frusto-conical portion 40 is as flared as possible in order to attempt to minimize the risks of contact with the droplets.

Moreover portion 41 is practically cylindrical so as to reduce the dimensions of the bell.

The degree of taper of portion 42 and of portion 41 are chosen to orientate the rebounds of the droplets as desired without the bell assuming dimensions that are too large.

The major proportion of the droplets which pass through the opening 51 is directly absorbed by the support (paths D and E) or rebounds slightly without coming back into contact with the device (path F).

However, where the rebound leads to a contact with the device (paths G and H), it will be noted that the annular portion 53 of the absorbent pad projecting inwardly of the bell makes it possible in that case to trap those droplets which then come back into contact with the absorbent pad and not into contact with the ring 6 of which the opening 61 is of greater diameter than that of the opening 51 for that reason (since in that case they then risk falling back onto the support, carrying extraneous ATP).

It can be noted that surface 82 and solely that surface receives the droplets of the jet, path D being the most extreme path possible. Beyond that, the droplets are captured by the pad such that no droplet risks coming into contact with the body 83 of the cassette 80 and then falling back onto the membrane 81, risking contaminating it with the extraneous ATP.

The support thus treated is then available for the microbiological analysis for example by moving the cassette 80 to the measuring station (not shown) within the same chamber in order to measure the quantity of light emitted in response to putting the reagent in contact with the ATP of the microorganisms that may be present on the membrane using a photomultiplier for example.

The device according to the invention may be used to treat several membranes, on each spraying operation the volume of liquid which was sprayed is replaced in the housing 17 by the air entering that housing through the pump 70.

It is also possible to regularly fill that housing by injecting a volume of reagent through the filter unit 23 using a syringe, the unit 22 forming a vent in that case.

Where the filter cassette is provided with a membrane of different diameter and thus of different useful surface, it is possible to adjust the distance separating that membrane from the pad 5 by moving the device 1 vertically in order for the jet of droplets to cover the whole of the surface of that membrane and solely that surface.

The device may be a single-use device but may also be used as many times as necessary provided that the pad is not saturated with liquid.

As a variant the spraying device may also be used in any microbiological analysis method requiring a pre-treatment step aimed at eliminating the extraneous ATP that the membrane contains by spraying that reagent on the membrane before having rendered the ATP of the microorganisms accessible (for example by lysis) in order for it to react and solely eliminate the extraneous ATP, it being possible to carry out the lysis step after neutralization of the sprayed reagent to eliminate the extraneous ATP.

In still another variant the spraying device may be used for any other type of reagent intended for microbiological analysis which it is sought to deposit uniformly over a surface while ensuring that the sprayed reagent is well confined.

The present invention is not limited to the embodiments described and represented but encompasses any variant form thereof.

The invention claimed is:

1. A method of spraying a reagent onto a support for the fast microbiological analysis of said support, said support being adapted to retain microorganisms on a predetermined surface, said method comprising:
    providing a spraying bell as well as a nozzle for emitting a jet of droplets of said reagent into a spraying chamber comprised by said bell;
    mounting an absorbent pad against said bell transversely to said jet and closing said chamber from the opposite side to said nozzle with the exception of a central opening provided in said pad, said central opening providing access to said support;
    emitting said jet of droplets from said nozzle towards said support, causing a portion of said jet, when said device faces said support and is at a predetermined distance therefrom, to pass through said central opening over its entire area and be deposited on the whole of said predetermined surface of said support.

2. The method of claim 1, wherein said jet of droplets has a periphery, and wherein said absorbent pad is positioned to collect the droplets at said periphery.

3. The method of claim 1, wherein said central opening has a diameter that is a function of the distance between said pad and said support.

4. The method of claim 1, wherein said absorbent pad comprises cellulose.

* * * * *